Sept. 16, 1952 E. S. BOERNER Plant Pat. 1,132
CHRYSANTHEMUM PLANT
Filed Sept 28, 1951
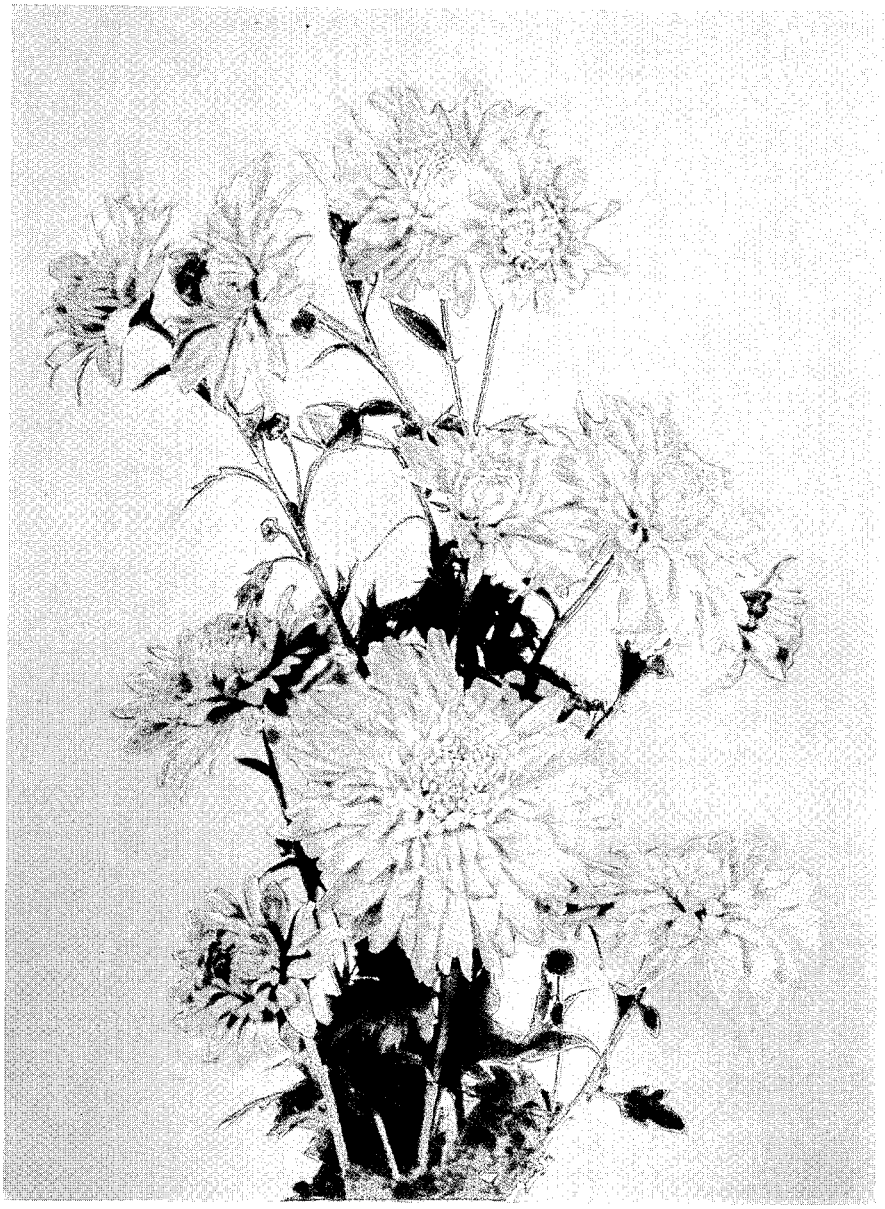
Inventor
E. S. Boerner
By: Robert Cobb
Attorneys.

Patented Sept. 16, 1952

Plant Pat. 1,132

UNITED STATES PATENT OFFICE 1,132

CHRYSANTHEMUM PLANT

Eugene S. Boerner, Newark, N. Y., assignor to Jackson & Perkins Company, Newark, N. Y., a corporation of New York Application September 28, 1951, Serial No. 248,794

1 Claim. (Cl. 47—60)

The present invention relates to a new and distinct variety of chrysanthemum plant, originated by me by crossing an unnamed and unpatented seedling of "Neta" × an unnamed and unpatented seedling of "Clara Curtis."

The primary objective of this cross was to produce a larger and hardier outdoor chrysanthemum of the "Clara Curtis" type. Accordingly, a very large-flowered seedling of "Neta," a semi-tender variety of orange color, was crossed by a seedling of "Clara Curtis," with the result that a new variety has been obtained which is vigorous, strong, upright and tall in its habits of growth, and bears flowers of a Deep Rose Pink color, lightly overcast with Rose color—something entirely different and unique in chrysanthemums.

In addition to the predominant pink color, its general characteristics are attributed to an infusion of "Clara Curtis" blood, with resultant unusual hardiness and early-blooming habit, commencing as early as August and continuing as late as October and November, after first frosts and until very heavy freezing in the up-State New York climatic area. These characteristics, together with its fullness and long persistence of bloom are very valuable and desirable in this new variety, particularly from a commercial standpoint.

Asexual reproduction of this new variety by top cuttings and by underground runners at Newark, New York, shows that the foregoing characteristics come true to form and are established and transmitted through succeeding propagations.

The accompanying drawing shows specimens of the new variety, with the flowers and foliage in different stages of development.

The following is a detailed description of the new variety, as observed in the fields at Newark, New York, in the early morning hours in the latter part of the month of September, with color terminology in accordance with Ridgway's Color Standards and Nomenclature:

Parentage: A seedling of "Neta" × a seedling of "Clara Curtis."
Classification: Semi-decorative type.
Growth: Strong; clean; upright; attaining a height of 3½ feet.
Cold resistance: Winter hardy in northern New York; flowers do not burn with early frosts.
Blooming period: Blooms start about August 15th in the Newark, New York, climatic area and continue until very heavy freezing in October and November.

Bud:
*Color.*—When sepals first divide—Eugenia Red, Plate 13. When petals begin to unfurl—Begonia Rose, Plate 1. When half blown—inside of petals: Deep Rose Pink, Plate 12, lightly overcast with Rose color, Plate 12; reverse of petals: Deep Rose Pink, Plate 12.
*Peduncle.*—Color—Cress Green, Plate 31. Strength—Stiff and slender.

Bloom:
*Size.*—4 inches.
*Stems.*—Long; narrow.
*Form.*—Semi-decorative type.
*Petalage.*—Very double.
*Color.*—Center of flower—Orange Buff, Plate 3, lightly tinted with Bittersweet Pink, Plate 2. Outer petals—Deep Rose Pink, Plate 12. Base of petals—Rose Pink, Plate 12. Inside of petals—Deep Rose Pink, Plate 12, lightly overcast with Rose color, Plate 12. Reverse of petals—Thulite Pink, Plate 26.
*Petals.*—Texture — stiff. Form — straight, with slight wavy ends.
*Fragrance.*—Characteristic chrysanthemum.

Plant:
*Form.*—Excellent; upright.
*Growth.*—Free.

Foliage:
*Size.*—Medium.
*Quantity.*—Normal.
*Color.*—Upper side—Bice Green, Plate 17. Reverse side—Light Bice Green, Plate 17.
*Texture.*—Leathery.

I claim:

A new and distinct variety of chrysanthemum plant, substantially as herein shown and described, characterized as to novelty by its vigorous, strong, upright, tall and free-blooming habits of growth, by its exceptional hardiness and its early-commencing and prolonged blooming habit, and by the predominant pink color of its semi-decorative type flowers.

EUGENE S. BOERNER.

No references cited.